(12) United States Patent
Xie et al.

(10) Patent No.: US 12,329,571 B2
(45) Date of Patent: Jun. 17, 2025

(54) METHOD AND APPARATUS FOR IDENTIFICATION OF IMAGING QUALITY OF FETAL ULTRASOUND IMAGES

(71) Applicant: GUANGZHOU AIYUNJI INFORMATION TECHNOLOGY CO., LTD., Guangdong (CN)

(72) Inventors: Hongning Xie, Guangdong (CN); Nan Wang, Guangdong (CN); Jianbo Xian, Guangdong (CN); Zhe Liang, Guangdong (CN); Jielin Wu, Guangdong (CN); Shuyu Liu, Guangdong (CN)

(73) Assignee: GUANGZHOU AIYUNJI INFORMATION TECHNOLOGY CO., LTD., Guangzhou (CN)

(*) Notice: Subject to any disclaimer, the term of this patent is extended or adjusted under 35 U.S.C. 154(b) by 165 days.

(21) Appl. No.: 18/126,363

(22) Filed: Mar. 24, 2023

(65) Prior Publication Data
US 2023/0233177 A1 Jul. 27, 2023

Related U.S. Application Data

(63) Continuation of application No. PCT/CN2021/096823, filed on May 28, 2021.

(30) Foreign Application Priority Data

Sep. 24, 2020 (CN) .......................... 202011015212.9

(51) Int. Cl.
*A61B 8/08* (2006.01)
(52) U.S. Cl.
CPC .. *A61B 8/0866* (2013.01); *G06T 2207/10132* (2013.01)

(58) Field of Classification Search
CPC .................. A61B 8/0866; G06T 2207/10132
See application file for complete search history.

(56) References Cited

U.S. PATENT DOCUMENTS

| | | | |
|---|---|---|---|
| 11,129,591 B2* | 9/2021 | Abolmaesumi | G06N 3/04 |
| 11,367,001 B2* | 6/2022 | Abolmaesumi | G06N 3/08 |

(Continued)

FOREIGN PATENT DOCUMENTS

| | | |
|---|---|---|
| CN | 108460765 A | 8/2018 |
| CN | 110464380 A | 11/2019 |

(Continued)

OTHER PUBLICATIONS

International Search Report of PCT Patent Application No. PCT/CN2021/096823 issued on Sep. 1, 2021.

*Primary Examiner* — Dixomara Vargas

(57) ABSTRACT

Disclosed in the present invention are a method and an apparatus for identification of imaging quality of fetal ultrasound images, the method including: acquiring parameters of fetal ultrasound images, used for identification of imaging quality of fetal ultrasound images; identifying an imaging score of fetal ultrasound images based on the parameters thereof; and identifying the imaging quality thereof based on the imaging score thereof. Obviously, it may lead to a quick and accurate identification of the imaging quality of fetal ultrasound images by automatically identifying the imaging quality thereof based on the imaging score thereof, thereby realizing quick and accurate management of the imaging quality thereof so as to facilitate to acquire fetal ultrasound images with high quality, which facilitates the acquisition of accurate fetal growth and development and may have an acknowledgment of the operational standardization of the personnel during the detection of fetal ultrasound images.

15 Claims, 3 Drawing Sheets

(56) References Cited

U.S. PATENT DOCUMENTS

| | | | | |
|---|---|---|---|---|
| 2011/0044524 | A1* | 2/2011 | Wang | G01R 33/5601 |
| | | | | 382/131 |
| 2020/0069292 | A1* | 3/2020 | Abolmaesumi | A61B 8/5207 |
| 2020/0214676 | A1* | 7/2020 | McLaughlin | G06T 5/50 |
| 2023/0181091 | A1* | 6/2023 | Yoo | A61B 5/7267 |
| | | | | 600/476 |
| 2023/0270409 | A1* | 8/2023 | Tanigawa | G16H 30/40 |
| | | | | 600/437 |
| 2024/0194340 | A1* | 6/2024 | Neumann | G16H 20/00 |
| 2024/0299002 | A1* | 9/2024 | Dhatt | G06N 3/045 |
| 2024/0310851 | A1* | 9/2024 | Ebrahimi Afrouzi | |
| | | | | A47L 9/2873 |

FOREIGN PATENT DOCUMENTS

| | | | |
|---|---|---|---|
| CN | 110604592 | A | 12/2019 |
| CN | 112070119 | A | 12/2020 |
| CN | 112215806 | A | 1/2021 |

\* cited by examiner

METHOD AND APPARATUS FOR IDENTIFICATION OF IMAGING QUALITY OF FETAL ULTRASOUND IMAGES

CROSS REFERENCE TO RELATED APPLICATIONS

The present application is a Continuation Application of PCT Application No. PCT/CN2021/096823 filed on May 28, 2021, which claims the benefit of Chinese Patent Application No. 202011015212.9 filed on Sep. 24, 2020. All the above are hereby incorporated by reference in their entirety.

FIELD OF THE INVENTION

The present invention relates to the technical field of image processing, and in particular to a method and apparatus for determining the imaging quality of fetal ultrasound images.

BACKGROUND OF THE INVENTION

As society progresses and people become more aware of the importance of having a healthy newborn, more pregnant women are going to the hospital for regular checkups to be informed of their baby's growth and development.

In practice, in order to clearly and accurately determine fetal growth and development, high-quality fetal ultrasound images are required, and in order to acquire high-quality fetal ultrasound images, it is necessary to identify the quality of fetal ultrasound images. Currently, the method for identification of imaging quality of the fetal ultrasound images is mainly based on the quantitative assessment of the fetal ultrasound images by medical personnel with relevant experience to determine whether or not the critical structures exist or the geometric shapes of the critical structures are standard. However, in practice, it has been found that the subjectivity and fatigue of the medical personnel after long working hours may easily lead to low accuracy in identifying the quality of the fetal ultrasound images.

SUMMARY OF INVENTION

The technical problem to be solved by the present invention is to provide a method and apparatus for identification of imaging quality of fetal ultrasound images, which may improve the identified accuracy for imaging quality of fetal ultrasound images.

In order to solve the above technical problems, as a first aspect, disclosed in the present invention is a method for identification of imaging quality of fetal ultrasound images, the method comprising: acquiring parameters of fetal ultrasound images, used for identification of imaging quality of fetal ultrasound images; identifying an imaging score for fetal ultrasound image based on the parameters thereof; and identifying the imaging quality thereof based on the imaging score thereof.

As an optional embodiment, in the first aspect of the present invention, the acquisition of the parameters of fetal ultrasound images comprises: inputting fetal ultrasound images into a predetermined parameter-identifying model for analysis and acquiring an analyzed result outputted by the parameter-identifying model as the parameters of fetal ultrasound images, the parameter-identifying model including a feature-identifying model and/or a cross-section-identifying model, wherein, for fetal ultrasound images, when the parameter-identifying model is the feature-identifying model, the parameters include featured parameters, the featured parameters include a part featured parameter and/or a structural featured parameter; when the parameter-identifying model is the cross-section-identifying model, the parameters include cross-sectional parameters, and the cross-sectional parameters include a cross-sectional score for a standard cross-section; and/or, receiving parameters regarding fetal ultrasound images sent by a predetermined terminal device and/or inputted by an authorized person as the parameters of ultrasound images, wherein, for fetal ultrasound images, the parameters include the featured parameters and/or cross-sectional parameters, the featured parameters include a part feature parameter and/or a structural feature parameter; and the cross-sectional parameters include a cross-sectional score for the standard cross-section.

As an optional embodiment, in the first aspect of the present invention, the fetal ultrasound images comprises multiple consecutive frames of fetal ultrasound sub-images; the identification of the imaging score for fetal ultrasound images based on the parameters thereof comprises: acquiring at least a targeted chapter by dividing the fetal ultrasound images into chapters, each targeted chapter comprising a plurality of consecutive frames of the fetal ultrasound sub-images, all the fetal ultrasound sub-images included in each targeted chapter differing from each other, a collective amount of all the fetal ultrasound sub-images included in each targeted chapter equaling to a collective amount of all the fetal ultrasound sub-images included in the fetal ultrasound images; computing a score for the targeted chapter based on parameters of targeted features of each frame of the fetal ultrasound sub-images included in each targeted chapter, for each frame of the fetal ultrasound sub-images, the targeted features comprising at least one of a part feature, a structural feature or a cross-sectional feature; and confirming the score for all the targeted chapters as the imaging score for the fetal ultrasound images.

As an optional embodiment, in the first aspect of the present invention, the fetal ultrasound images correspond to at least one targeted category, the targeted category comprising a feature category or a cross-sectional category, an amount of a targeted feature corresponding to each targeted category being greater than or equal to one; when the targeted category is the featured category, the targeted feature includes a part feature or a structural feature; when the targeted category is a cross-sectional category, the targeted feature includes a standard cross-section; and each of the targeted category corresponds to at least one frame of the fetal ultrasound sub-images, all the fetal ultrasound sub-images corresponding to each targeted category differing from each other, all the fetal ultrasound sub-images corresponding to all the targeted category constituting the fetal ultrasound images.

As an optional embodiment, in the first aspect of the present invention, division of the fetal ultrasound images into chapters and acquisition of at least a targeted chapter comprises: identifying, for each targeted category included in the fetal ultrasound images, a starting frame and an ending frame of the fetal ultrasound sub-images; confirming, for each targeted category, all the fetal ultrasound sub-images of the starting frame, the ending frame and all frames between the starting frame and the ending frame, as the targeted chapter corresponding to each targeted category; and for each targeted category corresponding to the fetal ultrasound sub-images, the starting frame of the fetal ultrasound sub-images is where the fetal ultrasound sub-images with the targeted feature of the targeted category first show in the fetal ultrasound images, and the ending frame of the fetal ultrasound sub-images is where the fetal ultrasound sub-images with the targeted feature of the targeted category last show in the fetal ultrasound images or where a predetermined amount of frames of the fetal ultrasound sub-images shows consecutively after the starting frame of the fetal ultrasound sub-images with the targeted feature of the targeted category.

As an optional embodiment, in the first aspect of the present invention, computation of the score for the targeted chapter based on the parameters of targeted features of each frame of the fetal ultrasound sub-images included in each targeted chapter comprises: computing a sum of the score for part features of each fetal ultrasound sub-image included in each targeted chapter, as the score for the targeted chapter, when the targeted feature, in each frame of the fetal ultrasound sub-images, is the part feature thereof; computing the score for the targeted chapter based on a probability of category, a probability of location and a weighted value for the structural feature of each frame of fetal ultrasound sub-images included in each targeted chapter, when the targeted feature, in each frame of the fetal ultrasound sub-images, is the structural feature thereof; and computing a sum of the score for cross-sections of the standard cross-section of each fetal ultrasound sub-image included in each targeted chapter, as the score for the targeted chapter, when the targeted feature, in each frame of the fetal ultrasound sub-images, is a standard cross-section thereof.

As an optional embodiment, in the first aspect of the present invention, after division of the fetal ultrasound images into chapters and acquisition of at least a targeted chapter, the method further comprises: identifying a total number of frames of the fetal ultrasound sub-images included in each targeted chapters; after computation of the score for the targeted chapter based on the parameters of targeted features of each frame of the fetal ultrasound sub-images included in each targeted chapter, the method further comprising: dividing the score for each targeted chapter by the total number of frames of all the fetal ultrasound sub-images included in the targeted chapter to acquire a targeted score for the targeted chapter; updating the score for each targeted chapter as the targeted score for the targeted chapter, and confirming the score for all the targeted chapters as the imaging score for the fetal ultrasound images.

As an optional embodiment, in the first aspect of the present invention, identification for the imaging score for the fetal ultrasound images based on the parameters thereof comprises: confirming the score for part features of the fetal ultrasound images as the imaging score thereof, when the parameter of the fetal ultrasound images is the part feature parameter thereof, the part feature parameter thereof comprising the score for part feature thereof; and/or, when the parameter of the fetal ultrasound images is the structural feature parameter thereof, the structural feature parameter thereof comprises the probability of category, the probability of location, and the weighted value of the structural feature thereof; computing the score for the structural feature based on the probability of category, the probability of location, and the weighted value of the structural feature of the fetal ultrasound images, and confirming the score for the structural feature as the imaging score for the fetal ultrasound images; and/or when the parameter of the fetal ultrasound images is the featured parameters thereof, the structural feature parameter thereof comprises the probability of category, the probability of location, and the weighted value of the structural feature thereof, and the part feature parameter thereof comprises a probability of category of the part feature of the fetal ultrasound images; computing the score for the structural feature based on the probability of category of the part feature, the probability of category, the probability of location, and the weighted value of the structural feature of the fetal ultrasound images, and confirming the score for the structural feature as the imaging score for the fetal ultrasound images; and/or, identifying the standard cross-section of the fetal ultrasound images based on the probability of category of the part feature, and the probability of category of the structural feature; and computing the cross-sectional score for the standard cross-section of the fetal ultrasound images based on the parameters of the structural features in the standard cross-section of the fetal ultrasound images as the imaging score for the fetal ultrasound images, the parameter of structural features of the fetal ultrasound images comprising the parameter of structural features in the standard cross-section of the fetal ultrasound images.

As an optional embodiment, in the first aspect of the present invention, before identification for the imaging quality of the fetal ultrasound images based on the imaging score thereof, the method further comprising: identifying a detecting result corresponding to the fetal ultrasound images, used for identification for the imaging quality of the fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections; and the identification for the imaging quality of the fetal ultrasound images based on the imaging score thereof comprises: identifying the imaging quality of the fetal ultrasound images based on combining the imaging score thereof and the detecting result corresponding to the fetal ultrasound images.

As a second aspect, disclosed in the present invention is an apparatus for identification of imaging quality of fetal ultrasound images, the apparatus comprising: an acquiring module, used for acquiring parameters of fetal ultrasound images, in which the parameter thereof is used for identification of imaging quality of fetal ultrasound images; a first identifying module, used for identifying an imaging score of fetal ultrasound images based on the parameters thereof; and a second identifying module, used for identifying the imaging quality of fetal ultrasound images based on the imaging score thereof.

As an optional embodiment, in the second aspect of the present invention, acquisition of the parameters of the fetal ultrasound images through the acquiring module comprising: inputting fetal ultrasound images into a predetermined parameter-identifying model for analysis and acquiring an analyzed result outputted by the parameter-identifying model as the parameters of fetal ultrasound images, the parameter-identifying model including a feature-identifying model and/or a cross-section-identifying model, wherein, for fetal ultrasound images, when the parameter-identifying model is the feature-identifying model, the parameters include featured parameters, the featured parameters include a part featured parameter and/or a structural featured parameter; when the parameter-identifying model is the cross-section-identifying model, the parameters include cross-sectional parameters, and the cross-sectional parameters include a cross-sectional score for a standard cross-section; and/or, receiving parameters regarding fetal ultrasound images sent by a predetermined terminal device and/or inputted by an authorized person as the parameters of ultrasound images, wherein, for fetal ultrasound images, the parameters include the featured parameters and/or cross-sectional parameters, the featured parameters include a part feature parameter and/or a structural feature parameter; and the cross-sectional parameters include a cross-sectional score for the standard cross-section.

As an optional embodiment, in the second aspect of the present invention, the fetal ultrasound images comprises multiple consecutive frames of fetal ultrasound sub-images; the first identifying module comprises: a dividing sub-module, used for dividing the fetal ultrasound images into chapters, and acquiring at least a targeted chapter, each targeted chapter comprising a plurality of consecutive frames of the fetal ultrasound sub-images, all the fetal ultrasound sub-images included in each targeted chapter differing from each other, a collective amount of all the fetal ultrasound sub-images included in each targeted chapter equaling to a collective amount of all the fetal ultrasound sub-images included in the fetal ultrasound images; a computing sub-module, used for computing a score for the targeted chapter based on parameters of targeted features of each frame of the fetal ultrasound sub-images included in each targeted chapter, for each frame of the fetal ultrasound sub-images, the targeted features comprising at least one of a part feature, a structural feature or a cross-sectional feature; and an confirming sub-module, used for confirming the score for all the targeted chapters as the imaging score for the fetal ultrasound images.

As an optional embodiment, in the second aspect of the present invention, the fetal ultrasound images correspond to at least one targeted category, the targeted category comprising a feature category or a cross-sectional category, an amount of a targeted feature corresponding to each targeted category being greater than or equal to one; when the targeted category is the featured category, the targeted feature includes a part feature or a structural feature; when the targeted category is a cross-sectional category, the targeted feature includes a standard cross-section; and each of the targeted category corresponds to at least one frame of the fetal ultrasound sub-images, all the fetal ultrasound sub-images corresponding to each targeted category differing from each other, all the fetal ultrasound sub-images corresponding to all the targeted category constituting the fetal ultrasound images.

As an optional embodiment, in the second aspect of the present invention, division of the fetal ultrasound images into chapters through the dividing sub-module, and acquisition of at least a targeted chapter comprises specifically: identifying, for each targeted category included in the fetal ultrasound images, a starting frame and an ending frame of the fetal ultrasound sub-images; confirming, for each targeted category, all the fetal ultrasound sub-images of the starting frame, the ending frame and all frames between the starting frame and the ending frame, as the targeted chapter corresponding to each targeted category; and for each targeted category corresponding to the fetal ultrasound sub-images, the starting frame of the fetal ultrasound sub-images is where the fetal ultrasound sub-images with the targeted feature of the targeted category first show in the fetal ultrasound images, and the ending frame of the fetal ultrasound sub-images is where the fetal ultrasound sub-images with the targeted feature of the targeted category last show in the fetal ultrasound images or where a predetermined amount of frames of the fetal ultrasound sub-images shows consecutively after the starting frame of the fetal ultrasound sub-images with the targeted feature of the targeted category.

As an optional embodiment, in the second aspect of the present invention, computation of the score for the targeted chapter through the computing sub-module based on the parameters of targeted features of each frame of the fetal ultrasound sub-images included in each targeted chapter comprises specifically: computing a sum of the score for part features of each fetal ultrasound sub-image included in each targeted chapter, as the score for the targeted chapter, when the targeted feature, in each frame of the fetal ultrasound sub-images, is the part feature thereof; computing the score for the targeted chapter based on a probability of category, a probability of location and a weighted value for the structural feature of each frame of fetal ultrasound sub-images included in each targeted chapter, when the targeted feature, in each frame of the fetal ultrasound sub-images, is the structural feature thereof; and computing a sum of the score for cross-sections of the standard cross-section of each fetal ultrasound sub-image included in each targeted chapter, as the score for the targeted chapter, when the targeted feature, in each frame of the fetal ultrasound sub-images, is a standard cross-section thereof.

As an optional embodiment, in the second aspect of the present invention, the confirming sub-module is further used for identification of a total number of frames of the fetal ultrasound sub-images included in each targeted chapters, after division of the fetal ultrasound images into chapters through the dividing sub-module and acquisition of at least a targeted chapter. The apparatus further comprises a computing module and an updating module; the computing module is used for dividing the score for each targeted chapter by the total number of frames of all the fetal ultrasound sub-images included in the targeted chapter to acquire a targeted score for the targeted chapter, after computation of the score for the targeted chapter through the first identifying module based on the parameters of targeted features of each frame of the fetal ultrasound sub-images included in each targeted chapter; and the updating module is used for updating the score for each targeted chapter as the targeted score for the targeted chapter, and triggering the second identifying module to confirm the score for all the targeted chapters as the imaging score for the fetal ultrasound images.

As an optional embodiment, in the second aspect of the present invention, identification for the imaging score for the fetal ultrasound images through the first identifying module based on the parameters thereof comprises specifically: confirming the score for part features of the fetal ultrasound images as the imaging score thereof, when the parameter of the fetal ultrasound images is the part feature parameter thereof, the part feature parameter thereof comprising the score for part feature thereof; and/or, when the parameter of the fetal ultrasound images is the structural feature parameter thereof, the structural feature parameter thereof comprises the probability of category, the probability of location, and the weighted value of the structural feature thereof; computing the score for the structural feature based on the probability of category, the probability of location, and the weighted value of the structural feature of the fetal ultrasound images, and confirming the score for the structural feature as the imaging score for the fetal ultrasound images; and/or when the parameter of the fetal ultrasound images is the featured parameters thereof, the structural feature parameter thereof comprises the probability of category, the probability of location, and the weighted value of the structural feature thereof, and the part feature parameter thereof comprises a probability of category of the part feature of the fetal ultrasound images; computing the score for the structural feature based on the probability of category of the part feature, the probability of category, the probability of location, and the weighted value of the structural feature of the fetal ultrasound images, and confirming the score for the structural feature as the imaging score for the fetal ultrasound images; and/or, identifying the standard cross-section of the fetal ultrasound images based on the probability of category of the part feature, and the probability of category of the structural feature; and computing the cross-sectional score for the standard cross-section of the fetal ultrasound images based on the parameters of the structural features in the standard cross-section of the fetal ultrasound images as the imaging score for the fetal ultrasound images, the parameter of structural features of the fetal ultrasound images comprising the parameter of structural features in the standard cross-section of the fetal ultrasound images.

As an optional embodiment, in the second aspect of the present invention, the apparatus further comprises: a third identifying module, used for, before identification for the imaging quality of the fetal ultrasound images through the second identifying module based on the imaging score thereof, identifying a detecting result corresponding to the fetal ultrasound images, used for identification for the imaging quality of the fetal ultrasound images, wherein the detecting result corresponding thereto comprises at least one of the results for features, biological diameters, and blood flow Doppler spectra, the feature detecting results comprising at least one of feature detecting results for parts, structures and standard cross-sections; and the identification for the imaging quality of the fetal ultrasound images through the second identifying module based on the imaging score thereof comprises specifically: identifying the imaging quality of the fetal ultrasound images based on combining the imaging score thereof and the detecting result corresponding to the fetal ultrasound images.

As a third aspect, disclosed in the present invention is another apparatus for identification of imaging quality of fetal ultrasound images, comprising a memory, memorized with an executable program; and a processor, coupled with the memory, wherein the processor, calling the executable program memorized in the memory, implements the method for identification of imaging quality of fetal ultrasound images disclosed by the first aspect in the present invention.

As a fourth aspect, disclosed in the present invention is a computer memory medium, which memorizes computer instructions used for calling for implementing a method for identification of imaging quality of fetal ultrasound images, disclosed by the first aspect in the present invention.

Compared with the prior art, there are beneficial effects of embodiments of the present invention as follows.

The embodiments of the present invention provide a method and apparatus for identification of imaging quality of fetal ultrasound images, the method comprising: acquiring parameters of fetal ultrasound images, used for identification of imaging quality of fetal ultrasound images; identifying an imaging score of fetal ultrasound images based on the parameters thereof; and identifying the imaging quality thereof based on the imaging score thereof. Obviously, it may lead to a quick and accurate identification of the imaging quality of fetal ultrasound images, by implementing the present invention, by identifying automatically the imaging quality thereof based on the imaging score thereof, thereby realizing a quick and accurate management of the imaging quality thereof so as to facilitate to acquire fetal ultrasound images with high quality, which facilitates the acquisition of accurate fetal growth and development, which may have an acknowledgment of the operational standardization of the personnel during the detection of fetal ultrasound images and may have an acknowledgment whether or not all the required detected items for fetus have been finished.

BRIEF DESCRIPTION OF THE DRAWINGS

In order to illustrate the technical solutions in the embodiments of the present invention more clearly, a brief description of the attached drawings required for the description of the embodiments is provided as follows. Obviously, the attached drawings in the following description are only some of embodiments of the present invention, and other attached drawings may be acquired based on these drawings without any inventive effort by a person of ordinary skill in the art.

DETAILED DESCRIPTION OF THE PREFERRED EMBODIMENTS

For facilitating a better understanding of the solution of the present invention by persons in the art, it will be described clearly and completely below in connection with the attached drawings in the embodiments of the present invention. Obviously, the embodiments described are only some of the embodiments of the present invention, and not all of them. All the other embodiments acquired without inventive efforts by those skilled in the art, based on the embodiments in the present invention, fall within the scope of protection of the present invention.

The terms "first", "second", and the like in the specification, the claims and the above-mentioned drawings of the present invention are used to identify different objects and are not intended to describe a particular sequence. In addition, the terms "comprise" and "include", and any derivatives and conjugations thereof, are intended to cover non-exclusive inclusion. For example, a process, method, apparatus, product, or device that comprises a series of steps or units is not limited to the listed steps or units, but optionally also comprises steps or units that are not listed, or optionally also comprises other steps or units that are inherent to those processes, methods, products, or devices.

The term "embodiment" herein means that a particular feature, structure or characteristic described in conjunction with an embodiment may be comprised in at least one embodiment of the present invention. The presence of the term in various places in the specification does not necessarily indicate the same embodiment, nor is it a separate or alternative embodiment that is mutually exclusive with other embodiments. It is understood, both explicitly and implicitly, by those skilled in the art that the embodiments described herein may be combined with other embodiments.

Disclosed in the present invention are a method and apparatus for identification of imaging quality of fetal ultrasound images. It may lead to a quick and accurate identification of the imaging quality of fetal ultrasound images, by identifying automatically the imaging quality thereof based on the imaging score thereof, thereby realizing a quick and accurate management of the imaging quality thereof so as to facilitate to acquire fetal ultrasound images with high quality, which facilitates the acquisition of accurate fetal growth and development, which may have an acknowledgment of the operational standardization of the personnel during the detection of fetal ultrasound images and may have an acknowledgment whether or not all the required detected items for fetus are completely finished. Detailed descriptions are provided as follows.

First Embodiment

Figure 1:
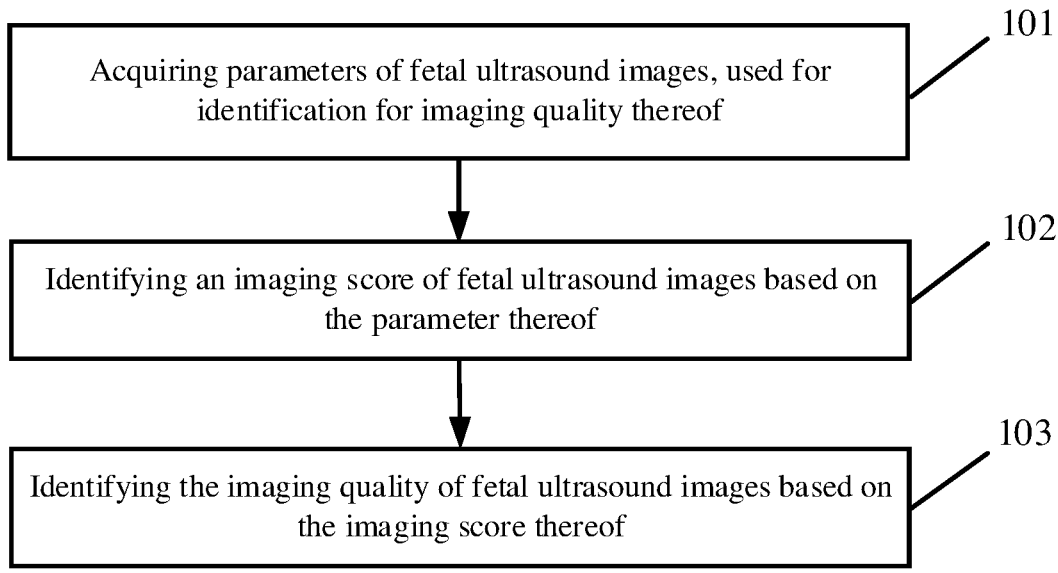
FIG. 1 is a process flow diagram of a method for identification of imaging quality of fetal ultrasound images, as disclosed in embodiments of the present invention.

Please refer to FIG. 1, which is a process flow diagram of the method for identification of imaging quality of fetal ultrasound images, as disclosed in embodiments of the present invention. As shown in FIG. 1, the method for identification of imaging quality of fetal ultrasound images may be applied in a server (service device) for identification of imaging quality, wherein the server therefor may include a local server therefor or a cloud server therefor, which is not limited herein. As shown in FIG. 1, the method for identification of imaging quality of fetal ultrasound images may comprise:

At step 101, acquiring parameters of fetal ultrasound images, used for identification of imaging quality of fetal ultrasound images.

In the present embodiment of the invention, a fetal ultrasound image is any fetal ultrasound image required to be identified for its imaging quality. Further, the fetal ultrasound image may be a picture of a single frame or a dynamic video. When the fetal ultrasound image is the picture of a single frame, for the fetal ultrasound images, the parameter may include a parameter of the single frame and further include a parameter corresponding to the video, which is not limited herein. The imaging quality of the fetal ultrasound images may indicate the imaging quality for the single frame or the video, which is not limited herein.

In the present embodiment of the invention, as an optional embodiment, the acquisition for the parameter of fetal ultrasound images may comprise: inputting fetal ultrasound images into a predetermined parameter-identifying model for analysis and acquiring an analyzed result outputted by the parameter-identifying model as the parameters of the fetal ultrasound images.

In the present embodiment of the invention, further and optionally, the fetal ultrasound images may be consecutively inputted into the parameter-identifying model for analysis by a predetermined frame rate (e.g., 30 frames per second) to acquire the analyzed result sequentially outputted by the parameter-identifying model as the parameters for each fetal ultrasound image, when the fetal ultrasound image is the picture of a single frame. It may facilitate the reduction of the occurrence of the failure to identify the imaging quality of the fetal ultrasound images due to insufficient or no parameters of the acquired fetal ultrasound images led by insufficient information on features included in a single frame of the fetal ultrasound images and facilitate to a quick acquisition for the parameter of the fetal ultrasound images, by inputting the consecutive multi-frame fetal ultrasound images into the parameter-identifying model for analysis. Alternatively, the fetal ultrasound images may be divided by the parameter-identifying model into multiple frames of the fetal ultrasound sub-images for analysis to acquire the parameter for the multiple frames thereof when the fetal ultrasound image is a dynamic video. It may improve the acquired possibility for the parameter of the fetal ultrasound images by handling the static or dynamic fetal ultrasound images through the aforementioned means.

In the present embodiment of the invention, further and optionally, there exists a unique corresponding frame number in the fetal ultrasound images. Each of the fetal ultrasound images may be clearly distinguished during the identified process of the imaging quality of the fetal ultrasound images by providing a unique frame number for each fetal ultrasound image, which may facilitate the management of the relevant information (e.g., imaging scores) of the fetal ultrasound images.

In the present embodiment of the invention, the parameter-identifying model includes a feature-identifying model and or a cross-section-identifying model, wherein, in the fetal ultrasound images, the feature-identifying model is a featured parameter identifiable model and the cross-section-identifying model is a cross-sectional parameter identifiable model. The parameter-identifying model may comprise a targeted detecting model, an instance splitting model, and a semantic splitting model, which may acquire parameters of the fetal ultrasound image, which is not limited herein.

In the present embodiment of the invention, when the parameter-identifying model is a feature-identifying model, for the fetal ultrasound images, the parameter includes the featured parameters, wherein the featured parameters include the part featured parameter and/or structural featured parameter.

In the present embodiment of the invention, for the fetal ultrasound images, the part featured parameter includes the category and the possibility of the category (also known as confidence level) of the part feature. Further, for the fetal ultrasound images, the part featured parameter may comprise graphical coordinates of the part feature.

In the present embodiment of the invention, for the fetal ultrasound images, the structural featured parameter includes the category and the possibility of the category (also known as confidence level) of the structural feature. Further, for the fetal ultrasound images, the structural featured parameter includes at least one of the graphical coordinates, dimensions, and location possibility of the structural feature, which is not limited herein. Further, for the fetal ultrasound images, the structural featured parameter includes a parameter of polygonal contours, such as polygonal contour coordinate; the more content the structural featured parameter of the fetal ultrasound images includes, the more facilitate to improve the identified accuracy and identified efficiency of the imaging quality of the fetal ultrasound images.

In the present embodiment of the invention, the graphical coordinate of the aforementioned part feature or structural feature may comprise a polygonal coordinate or an elliptical coordinate, and a polygonal coordinate may comprise an odd polygonal coordinate or an even polygonal coordinate, which is exemplified by: a pentagonal coordinate, a rectangular coordinate. The polygon coordinate is identified by the shape of the part feature or structural feature, which may improve the acquired accuracy of the coordinate for the part feature and structural feature.

In the present embodiment of the invention, when the parameter-identifying model is a cross-section-identifying model, for the fetal ultrasound images, the parameter includes a cross-sectional parameter, wherein the cross-sectional parameters include the cross-sectional score of the standard cross-section. Further, for the fetal ultrasound images, the cross-sectional parameters include the cross-sectional category of the standard cross-section. It may improve the acquired efficiency and acquired accuracy of the cross-sectional parameter of the fetal ultrasound images by automatically acquiring the cross-sectional parameter thereof through the cross-section-identifying model.

Obviously, the implementation of the present embodiment of the invention may quickly, without manual involvement, realize the automated acquisition for the parameter of the fetal ultrasound images by inputting the fetal ultrasound images into the parameter-identifying model for analysis, which may improve the acquired accuracy and acquired reliability for the parameter of the fetal ultrasound images, thereby improving the identified accuracy and identified efficiency for the imaging score of the fetal ultrasound images.

In the present embodiment of the invention, as an optional embodiment, the acquisition for the parameter of the fetal ultrasound images may comprise: receiving parameters regarding fetal ultrasound images sent by a predetermined terminal device and/or inputted by an authorized person as the parameters of fetal ultrasound images.

In the present embodiment of the invention, for fetal ultrasound images, the parameters include the featured parameters and/or cross-sectional parameters, the featured parameters include a part feature parameter and/or a structural feature parameter; and the cross-sectional parameters include a cross-sectional score for the standard cross-section.

In the present embodiment of the invention, it is to be noted that, regarding the other description for the parameter of the fetal ultrasound images, please refer to the detailed description therefor in the aforementioned embodiments, which is not repeated hereby.

In the present embodiment of the invention, the terminal device communicates in advance with the imaging quality identifying server (service device).

Obviously, in the present embodiment of the invention, it may enrich the acquisition means for the parameter of the fetal ultrasound images by acquiring the parameter thereof sent by the terminal device and/or inputted by the authorized personnel.

In the present embodiment of the invention, it is to be noted that the parameter of the fetal ultrasound images may be acquired through the aforementioned means, which may enrich the acquisition means for the parameter of the fetal ultrasound images, so as to improve the acquired possibility for the parameter thereof; it may improve the acquired accuracy for the imaging score thereof by acquiring the imaging score thereof through combining the featured parameters and cross-sectional parameter thereof.

At step 102, identifying an imaging score of fetal ultrasound images based on the parameters thereof.

In the present embodiment of the invention, the aforementioned fetal ultrasound images comprises multiple consecutive frames of fetal ultrasound sub-images; as an optional embodiment, the identification of the imaging score for fetal ultrasound images based on the parameters thereof may comprise: dividing the fetal ultrasound images into chapters, and acquiring at least a targeted chapter; computing a score for the targeted chapter based on parameters of targeted features of each frame of the fetal ultrasound sub-images included in each targeted chapter, and confirming the score for all the targeted chapters as the imaging score for the fetal ultrasound images.

In the present embodiment of the invention, optionally, the targeted feature of each frame of the fetal ultrasound sub-images includes at least one of part features, structural features, and standard cross-sections of the fetal ultrasound sub-images.

In the present embodiment of the invention, the part features of the fetal ultrasound sub-images include but are not limited to abdominal, craniocerebral, pulmonary, arms, toe, and cardiac features.

In the present embodiment of the invention, the structural features of the fetal ultrasound sub-images include but are not limited to the structural feature of the gastric vacuole, umbilical vein, cavum septum pellucidum, thalamus, lateral ventricles, liver, descending aorta, humerus, and inferior vena cava.

In the present embodiment of the invention, the cross-sectional features of the fetal ultrasound sub-images include but are not limited to the cross-section for measuring crown-rump length, measuring biparietal diameter, measuring nuchal translucency (NT), mid-sagittal view of face, measuring frontomaxillary facial angle, measuring humeral length, measuring femoral length, bilateral upper limbs, bilateral lower extremity, measuring fetal heart rate, measuring spectrum of tricuspid valve, measuring spectrum of ductus venosus, gastric vacuole, bladder, bilateral umbilical arteries, showing gender, measuring nasal bone, measuring inner diameter of intestine, long-diameter of the radius and ulna, middle cerebral artery, umbilical vein of the gallbladder, ductus arteriosus, pulmonary vein into the left atrium, abdominal circumference, anus, long-diameter of humerus, measuring cervix, long-diameter of femur, coronary sinus, locating conus medullaris, coronal view of the spine, spine, long-diameter of tibia and fibula, nuchal fold (NF), bladder and bilateral umbilical arteries, measuring spectrum of umbilical artery, umbilical cord insertion into the placenta, umbilical cord wrapping around the neck, umbilical cord entrance, three vessel and trachea, superior and inferior vena cava into the right atrium, upper tooth-bearing alveolar process, measuring the long-diameter of kidney, esophagus and trachea, arms, biparietal diameter, transverse view of both kidney, four-chambered heart, placenta, mid-sagittal view of head, head through the vagina, cerebellum, thorax and abdomen, appearance of facial surface, measuring interocular distance, amniotic fluid volume, right ventricular outflow tract, aortic arch, feet, left saphenous vein joining the right superior vena cava, left ventricular outflow tract, bifurcations of left and right pulmonary artery, and ears.

In the present embodiment of the invention, the targeted features of each fetal ultrasound sub-images comprise cross-sections with at least one orientation, wherein the orientation includes a horizontal one, a sagittal one, and a coronal one, which is exemplified by that: an abdominal feature includes a horizontal view of the abdominal feature, a sagittal view of the abdominal feature, and a coronal view of the abdominal feature; a cross-section of the abdominal circumference includes a horizontal view of the cross-section of the abdominal circumference, a sagittal view of the cross-section of the abdominal circumference, and a coronal view of the cross-section of the abdominal circumference; and a structural feature of the gastric vacuole includes a horizontal view of the structural feature of the gastric vacuole, a sagittal view of the structural feature of the gastric vacuole, and a coronal view of the structural feature of the gastric vacuole.

In the present embodiment of the invention, each targeted chapter comprises a plurality of consecutive frames of the fetal ultrasound sub-images, all the fetal ultrasound sub-images included in each targeted chapter differing from each other, a collective amount of all the fetal ultrasound sub-images included in each targeted chapter equaling to a collective amount of all the fetal ultrasound sub-images included in the fetal ultrasound images.

In the present embodiment of the invention, division of the fetal ultrasound images into chapters may be instantaneous, that is, inputting fetal ultrasound images into a predetermined parameter-identifying model for analysis and acquiring an analyzed result outputted by the parameter-identifying model as the parameters of fetal ultrasound images, while dividing all the fetal ultrasound sub-images into chapters. The division of the fetal ultrasound sub-images into chapters may also be implemented after ultimately acquiring all the parameters of the fetal ultrasound sub-images, which is not limited herein.

In the present embodiment of the invention, further and optionally, the aforementioned fetal ultrasound images correspond to at least one targeted category, the targeted category comprising a feature category or a cross-sectional category, an amount of a targeted feature corresponding to each targeted category being greater than or equal to one;

when the targeted category is the featured category, the targeted feature includes a part feature or a structural feature;

when the targeted category is a cross-sectional category, the targeted feature includes a standard cross-section; and each of the targeted category corresponds to at least one frame of the fetal ultrasound sub-images, all the fetal ultrasound sub-images corresponding to each targeted category differing from each other, all the fetal ultrasound sub-images corresponding to all the targeted category constituting the fetal ultrasound images.

Obviously, in the present embodiment of the invention, computing the score of each chapter as the imaging score of the fetal ultrasound image by automatically dividing the fetal ultrasound images into chapters with different categories, which may improve the acquired accuracy and acquired efficiency for the imaging score of the fetal ultrasound images, so as to facilitate to improve the identified accuracy and identified reliability for the imaging quality thereof, thereby realizing a quick and accurate management of the imaging quality thereof so as to facilitate to acquire fetal ultrasound images with high quality, which facilitates the acquisition of accurate fetal growth and development.

In the optional embodiment, further and optionally, division of the fetal ultrasound images into chapters and acquisition of at least a targeted chapter may comprise: identifying, for each targeted category included in the fetal ultrasound images, a starting frame and an ending frame of the fetal ultrasound sub-images; confirming, for each targeted category, all the fetal ultrasound sub-images of the starting frame, the ending frame and all frames between the starting frame and the ending frame, as the targeted chapter corresponding to each targeted category.

In the present embodiment of the invention, for each targeted category corresponding to the fetal ultrasound sub-images, the starting frame of the fetal ultrasound sub-images is where the fetal ultrasound sub-images with the targeted feature of the targeted category first show in the fetal ultrasound images, and the ending frame of the fetal ultrasound sub-images is where the fetal ultrasound sub-images with the targeted feature of the targeted category last show in the fetal ultrasound images or where a predetermined amount of frames of the fetal ultrasound sub-images shows consecutively after the starting frame of the fetal ultrasound sub-images with the targeted feature of the targeted category, which facilitates to improve the identified accuracy for the ending frame of the fetal ultrasound images corresponding to each targeted category, so as to improve the identified accuracy for the targeted chapter of each targeted category, thereby improving the identified accuracy for the score of the targeted chapter. It is to be noted that a situation also applies to the instantaneous division of the fetal ultrasound images into chapters, wherein the situation is that the ending frame of the fetal ultrasound sub-images is where a predetermined amount of frames of the fetal ultrasound sub-images shows consecutively after the starting frame of the fetal ultrasound sub-images with the targeted feature of the targeted category.

For example, the targeted category is the category of a structural feature of gastric vacuole; the fetal ultrasound images include 100 frames of the fetal ultrasound sub-images; the structural feature of the gastric vacuole first shows at the fifth frame of the fetal ultrasound sub-images and last shows at the fiftieth frame of the fetal ultrasound sub-images, so, for the category of the structural feature of gastric vacuole corresponding to the fetal ultrasound sub-images, the starting frame is the fifth frame, and the ending frame is the fiftieth frame; or, the predetermined amount of frames corresponding to the category of a structural feature of the gastric vacuole is thirty, that is, the ending frame of the fetal ultrasound sub-images is thirty frames shows consecutively after the fifth frame (i.e., the thirty-fourth frame).

As another example, the targeted category is the standard cross-section of abdominal circumference; the fetal ultrasound images include 100 frames of the fetal ultrasound sub-images; the standard cross-section of abdominal circumference first shows at the fifth frame of the fetal ultrasound sub-images and last shows at the fiftieth frame of the fetal ultrasound sub-images, so, for the standard cross-section of abdominal circumference corresponding to the fetal ultrasound sub-images, the starting frame is the fifth frame, and the ending frame is the fiftieth frame; or, the predetermined amount of frames corresponding to the standard cross-section of abdominal circumference is thirty, that is, the ending frame of the fetal ultrasound sub-images is thirty frames shows consecutively after the fifth frame (i.e., the thirty-fourth frame).

In the present embodiment of the invention, all the fetal ultrasound sub-images included in the targeted chapter corresponding to each targeted category comprise at least the fetal ultrasound images including the targeted feature of the targeted category; the amount of the targeted feature of the targeted category included in the targeted chapter corresponding to each targeted category is greater than or equal to one. Further, all the fetal ultrasound sub-images included in the targeted chapter corresponding to each targeted category comprise the fetal ultrasound sub-images excluding the targeted feature of the targeted category. For example, the chapter corresponding to the category of the structural feature of gastric vacuole comprises fifty frames of fetal ultrasound images, wherein there are forty-five frames of the fetal ultrasound sub-images corresponding to the category of the structural feature of the gastric vacuole, and the other five frames of the fetal ultrasound sub-images comprise the structural feature of fingers.

Obviously, in the present embodiment of the invention, it may realize the automated identification of the chapter corresponding to each part feature, structural feature, or standard cross-section by automatically identifying each part feature, structural feature, or standard cross-section in the fetal ultrasound images a starting frame and an ending frame, which facilitates to improve the identified efficiency and identified accuracy for each chapter, so as to facilitate to improve the computed efficiency and computed accuracy for the score of each chapter.

In the optional embodiment, further and optionally, computation of the score for the targeted chapter based on the parameters of targeted features of each frame of the fetal ultrasound sub-images included in each targeted chapter comprises:

computing a sum of the score for part features of each fetal ultrasound sub-image included in each targeted chapter, as the score for the targeted chapter, when the targeted feature, in each frame of the fetal ultrasound sub-images, is the part feature thereof;

computing the score for the targeted chapter based on a probability of category, a probability of location and a weighted value for the structural feature of each frame of fetal ultrasound sub-images included in each targeted chapter, when the targeted feature, in each frame of the fetal ultrasound sub-images, is the structural feature thereof; and computing a sum of the score for cross-sections of the standard cross-section of each fetal ultrasound sub-image included in each targeted chapter, as the score for the targeted chapter, when the targeted feature, in each frame of the fetal ultrasound sub-images, is a standard cross-section thereof.

In the present embodiment of the invention, when the targeted feature of each fetal ultrasound sub-image is the structural feature of the fetal ultrasound sub-images, the formula for computing the score for the targeted chapter corresponding to each feature category is as follows:

$$S_1 = \Sigma_{i=1}^{M} H_i;$$

$$H_i = P_i \times Q_i \times O_i;$$

$S_1$ is the score of the targeted chapter corresponding to each feature category. Corresponding to the feature category in the targeted chapter, $H_i$ is the score of the $i^{th}$ structural feature, M is the total amount of the structural features, $P_i$ is the confidence level of the $i^{th}$ structural feature, $Q_i$ is the location possibility of the $i^{th}$ structural feature, $O_i$ is the weighted value of the $i^{th}$ structural feature.

In the present embodiment of the invention, the parameter of the structural feature of each frame of fetal ultrasound image included in each targeted chapter further includes the probability of the part where the structural features are located, while the formula for computing the score for the $i^{th}$ structural feature corresponding to the feature category included in the targeted chapter is as follows:

$$H_i = P_i \times Q_i \times O_i \times C_i;$$

Corresponding to the feature category included in the targeted chapter, $C_i$ is the probability of the part where the $i^{th}$ structural feature is located. The more parameters of the structural features there are, the more facilitate to improve the computed accuracy of the scores for the structural features, which facilitates to further improve the accuracy of scores for the chapters corresponding to the structural features, thereby further improving the identified accuracy of the imaging quality of the fetal ultrasound image.

In the optional embodiment, when the targeted feature of each frame of the fetal ultrasound sub-image is the standard cross-section of the fetal ultrasound sub-image, the formula for computing the score for the chapter corresponding to each cross-sectional category is as follows:

$$S_2 = \Sigma_{j=1}^{N} K_j;$$

$S_2$ is the score of the targeted chapter corresponding to each cross-sectional category, N is the total amount of the standard cross-sections corresponding to the cross-sectional category included in the targeted chapter, $K_j$ is the cross-sectional score of the $j^{th}$ standard cross-section corresponding to the cross-sectional category included in the targeted chapter.

In the optional embodiment, when the targeted feature of each frame of the fetal ultrasound sub-image is the part feature of the fetal ultrasound sub-image, the formula for computing the score for the targeted chapter corresponding to each part category is as follows:

$$S_3 = \Sigma_{k=1}^{D} W_k;$$

$S_3$ is the score for the targeted chapter corresponding to each part category, D is the total amount of the part features corresponding to the part category included in the targeted chapter, $W_k$ is the score for the $k^{th}$ part feature corresponding to the part category included in the targeted chapter.

In the present embodiment of the invention, further and optionally, for the targeted feature of each fetal ultrasound sub-image includes one or more features in horizontal orientation, sagittal one, and coronal one, the score for each targeted chapter may include the average of at least one orientation of the three orientations of the targeted feature of the corresponding targeted category. For example, when the structural feature included in chapter A is the gastric vacuole, computing the score for the structural feature corresponding to the horizontal orientation, the sagittal one, and the coronal one of each gastric vacuole included in chapter A, and further computing the average score for the structural feature corresponding to the three orientations of the gastric vacuole as the score of the chapter A. For the computing means for the average score for multiple orientations of part features or standard cross-section, please refer to computing means for the average score for multiple orientations of structural features, which is identical and not repeated hereby. Computing the average score for multiple orientations of structural features, part features, and standard cross-section as the score of the chapter, may further improve the computed accuracy of the score of the chapter, which further improves the identified accuracy of the imaging quality of the fetal ultrasound images, thereby facilitating to acquire the fetal ultrasound images with high quality.

Obviously, in the present embodiment of the invention, not only may the identification of the score for the chapter be realized, but also may the identified means of the score for the chapter be enriched, which improves the identified accuracy and identified reliability of the score for the chapter. The imaging quality of the fetal ultrasound images is confirmed by combining the scores for the chapter computed by the scores of structural features, part features, and cross-section, which may further improve the confirmed accuracy and confirmed reliability of the imaging quality of the fetal ultrasound images, thereby further facilitating to acquire the fetal ultrasound images with higher quality.

In the present embodiment of the invention, since each standard cross-section includes at least one structural feature, besides being acquired from at least one of the means of sending by the aforementioned terminal device, inputting by authorized personnel or outputting by the cross-section identifying model, the cross-sectional score of each standard cross-section may also be acquired through computing the score for each structural feature included in the standard cross-section, that is, computing the score of each category of the standard cross-section based on the score of each structural feature included in each standard cross-section of each category of the standard cross-section. Computing the average of the score for the chapter computed by the cross-sectional score of each category of the standard cross-section and the score for the chapter acquired directly by the cross-sectional score of each category of the standard cross-section as the final score for the chapter. For example, the targeted category of cross-section corresponding to chapter B is the cross-section of abdominal circumference; five cross-sections of the abdominal circumference are included in chapter B, wherein the scores for each cross-section of the abdominal circumference are respectively 10, 8, 9, 9.5, and 8.6; the score for chapter B computed by the scores for the cross-sections of the abdominal circumference is 45.1. The structural features of the cross-section of the abdominal circumference include the gastric vacuole with a score for the structural feature of 14.5, the umbilical vein with a score for the structural feature of 16, and the liver with a score for the structural feature of 15.5; then the score of the chapter B computed by the scores for structural features is 46. Computing the average of 45.1 and 46 as the final score of the chapter B, which equals to 45.55. Computing the average of the scores of the chapter acquired from different means as the final score of the chapter, that is, the imaging score of the fetal ultrasound images, which may further improve the identified accuracy for the imaging score of the fetal ultrasound images, thereby further improving the confirmed accuracy for the imaging quality of the fetal ultrasound images.

In the present embodiment of the invention, further, the part feature includes multiple standard cross-sections, standard cross-sections including multiple structural features. when the score of the chapter corresponding to the part feature is computed, computing the average score of the chapter computed by the cross-sectional score of multiple standard cross-sections and the score of the chapter corresponding to the structural feature as the final score of the chapter. For an illustrative example, please refer to the detailed description of the score relationship between the standard cross-section and the structural features included in the standard cross-section in the previous example, which is not repeated hereby.

In an optional embodiment, after division of the fetal ultrasound images into chapters and acquisition of at least a targeted chapter, the method further comprises: identifying a total number of frames of the fetal ultrasound sub-images included in each targeted chapters; after computation of the score for the targeted chapter based on the parameters of targeted features of each frame of the fetal ultrasound sub-images included in each targeted chapter, the method further comprising: dividing the score for each targeted chapter by the total number of frames of all the fetal ultrasound sub-images included in the targeted chapter to acquire a targeted score for the targeted chapter; updating the score for each targeted chapter as the targeted score for the targeted chapter, and implementing the step 103.

For example, the chapter corresponding to the category for the structural feature of the gastric vacuole includes 100 frames of the fetal ultrasound images; the score for the chapter corresponding to the category for the structural feature of the gastric vacuole is 180; then dividing 180 by 100 to have 1.8 as the score for the chapter; and updating 1.8 as the score for the chapter corresponding to the category for the structural feature of the gastric vacuole.

Obviously, in the optional embodiment, after acquiring the score of the chapter, acquiring a new score of the chapter further based on the score of the chapter and the total frames of the chapter and updating the new score as the imaging score of the fetal ultrasound images, which may further improve the identified accuracy for the imaging score of the fetal ultrasound images, so as to facilitate to improve the identified accuracy for the imaging quality of the fetal ultrasound images.

In the present embodiment of the invention, as an optional embodiment, identification for the imaging score for the fetal ultrasound images based on the parameters thereof comprises: confirming the score for part features of the fetal ultrasound images as the imaging score thereof, when the parameter of the fetal ultrasound images is the part feature parameter thereof, the part feature parameter thereof comprising the score for part feature thereof; and/or, when the parameter of the fetal ultrasound images is the structural feature parameter thereof, the structural feature parameter thereof comprises the probability of category, the probability of location, and the weighted value of the structural feature thereof; computing the score for the structural feature based on the probability of category, the probability of location, and the weighted value of the structural feature of the fetal ultrasound images, and confirming the score for the structural feature as the imaging score for the fetal ultrasound images; and/or when the parameter of the fetal ultrasound images is the featured parameters thereof, the structural feature parameter thereof comprises the probability of category, the probability of location, and the weighted value of the structural feature thereof, and the part feature parameter thereof comprises a probability of category of the part feature of the fetal ultrasound images; computing the score for the structural feature based on the probability of category of the part feature, the probability of category, the probability of location, and the weighted value of the structural feature of the fetal ultrasound images, and confirming the score for the structural feature as the imaging score for the fetal ultrasound images; and/or, identifying the standard cross-section of the fetal ultrasound images based on the probability of category of the part feature, and the probability of category of the structural feature; and computing the cross-sectional score for the standard cross-section of the fetal ultrasound images based on the parameters of the structural features in the standard cross-section of the fetal ultrasound images as the imaging score for the fetal ultrasound images, the parameter of structural features of the fetal ultrasound images comprising the parameter of structural features in the standard cross-section of the fetal ultrasound images.

Obviously, in the present embodiment of the invention, realizing the computation for the score of the fetal ultrasound images by respectively computing the score for part features, structural features, and standard cross-sections thereof, which may enrich the identification means for the score thereof, so as to improve the identified accuracy for the imaging quality thereof, thereby further realizing quick and accurate management of the imaging quality thereof.

At step 103, identifying the imaging quality of fetal ultrasound images based on the aforementioned imaging score thereof.

In the present embodiment of the invention, further and optionally, saving the imaging score of the fetal ultrasound images, so as to facilitate to optimize the imaging quality identifying server based on the imaging score, thereby further facilitating to acquire the fetal ultrasound images with high quality.

In the present embodiment of the invention, the structural feature of the standard cross-section of the fetal ultrasound image comprises at least a critical structural feature of the standard cross-section and further comprises other structural features. Identifying whether the standard cross-section is a normal standard cross-section or a suspected cross-section based on the structural feature included in the standard cross-section, after acquiring the standard cross-section of the fetal ultrasound images, which is exemplified by that: in the cross-section of abdominal circumference, the gastric vacuole and umbilical vein are critical structural features, whereas the liver, descending aorta, rib, and inferior vena cava are other structural features; if in the cross-section of the abdominal circumference are included critical structural features like the gastric vacuole and umbilical vein and also other structural features like the liver, descending aorta, rib, and inferior vena cava, the cross-section of the abdominal circumference is a normal standard cross-section; if in the cross-section of the abdominal circumference are included critical structural features like the gastric vacuole and umbilical vein but excluded other structural features like the liver, descending aorta, rib, and inferior vena cava, the cross-section of the abdominal circumference is a suspected standard cross-section.

Obviously, the implementation of the method for identification of imaging quality of fetal ultrasound images, as described in FIG. 1, may lead to a quick and accurate identification of the imaging quality of fetal ultrasound images, by implementing the present invention, by identifying automatically the imaging quality thereof based on the imaging score thereof, thereby realizing a quick and accurate management of the imaging quality thereof so as to facilitate to acquire fetal ultrasound images with high quality, which facilitates the acquisition of accurate fetal growth and development, which may have an acknowledgment of the operational standardization of the personnel during the detection of fetal ultrasound images and may have an acknowledgment whether or not all the required detected items for fetus have been finished.

Second Embodiment

Figure 2:
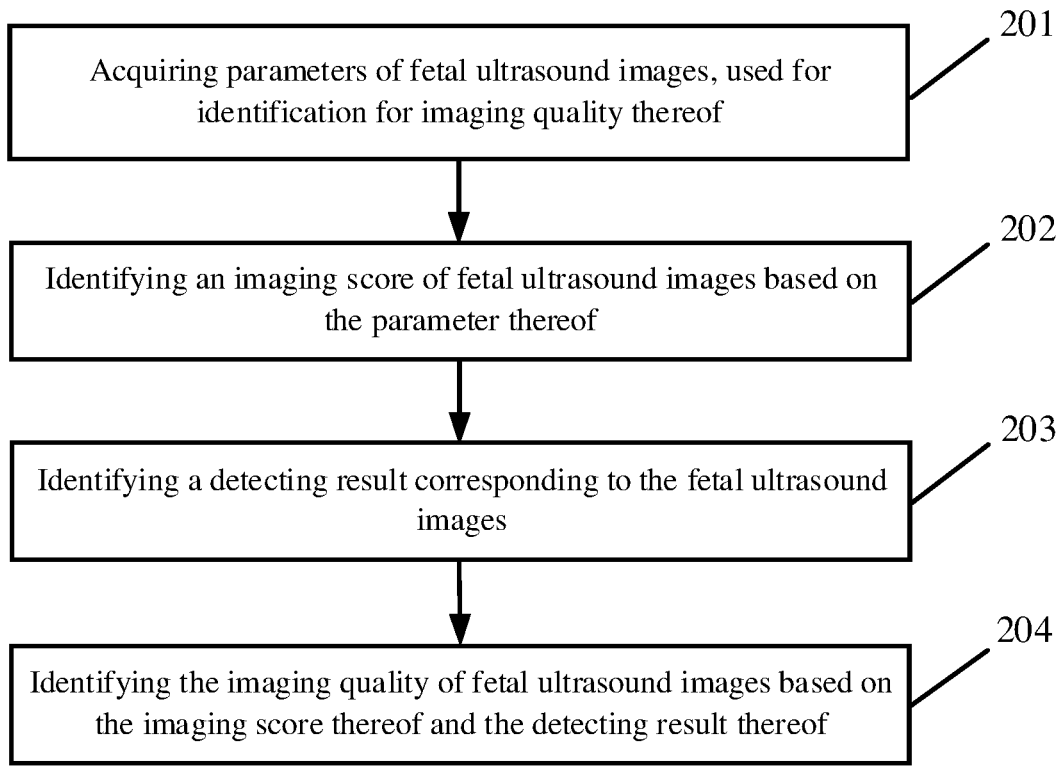
FIG. 2 is a process flow diagram of another method for identification of imaging quality of fetal ultrasound images, as disclosed in embodiments of the present invention.

Please refer to FIG. 2, which is another process flow diagram of the method for identification of imaging quality of fetal ultrasound images, as disclosed in embodiments of the present invention. As shown in FIG. 2, the method for identification of imaging quality of fetal ultrasound images may be applied in a server (service device) for identification of imaging quality, wherein the server therefor may include a local server therefor or a cloud server therefor, which is not limited herein. As shown in FIG. 2, the method for identification of imaging quality of fetal ultrasound images may comprise:

At step 201, acquiring parameters of fetal ultrasound images, used for identification of imaging quality of fetal ultrasound images.

At step 202, identifying an imaging score of fetal ultrasound images based on the parameters thereof.

At step 203, identifying a detecting result corresponding to the fetal ultrasound images.

In the present embodiment of the invention, the detecting result corresponding thereto is used for identification for imaging quality of fetal ultrasound images, wherein the detecting result corresponding thereto comprises at least one of detecting results for features, biological diameters, and Doppler blood flow spectra, the feature detecting results comprising at least one of feature detecting results for parts, structures and standard cross-sections, which is not limited herein.

In the present embodiment of the invention, the feature detecting results are used for determining whether or not all the required detected features have been finished, that is, determining whether or not at least one of the required detected features of part, structure, and standard cross-section has been finished.

In an optional embodiment, after implementing the step 203, the method may further comprise: determining whether or not the detecting result corresponding to the aforementioned fetal ultrasound images satisfies the predetermined detecting requirements; when the determination result is positive, implementing the step 204; when the determination result is negative, generating a detecting reminder for the fetal ultrasound images, and outputting the detecting reminder.

In the optional embodiment, the detecting reminder is used for reminding at least one of the presences of undetected features (e.g., the cross-section of the long-diameter of the humerus is undetected), undetected biological diameters of the fetal ultrasound images, and undetected blood flow Doppler spectra thereof. The detecting reminder is used for reminding authorized personnel to implement the detection of undetected items.

In the optional embodiment, optionally, after outputting the detecting reminder, the step 204 may be implemented.

Obviously, in the optional embodiment, after acquiring the detecting result of the fetal ultrasound images, determining first whether or not the detecting result satisfies the detecting requirements, when satisfies, implementing the subsequent confirmation for the imaging quality of the fetal ultrasound images, when not satisfies, outputting the detecting reminder of the fetal ultrasound images, which may remind the authorized personnel the presence of undetected items and supervise the operations and actions of the authorized personnel, which facilitates the authorized personnel to detect the undetected items, which facilitates to acquire an accurate imaging score of the fetal ultrasound images, so as to improve the identified accuracy of the imaging quality of the fetal ultrasound images, thereby realizing quick and accurate management of the imaging quality.

Obviously, in the present embodiment of the invention, identifying the imaging quality of the fetal ultrasound images based on combining the imaging score thereof and the detecting result corresponding to the fetal ultrasound images by acquiring the detecting result thereof, such as whether or not all the required detected standard cross-sections have been detected, which may further improve the identified accuracy for the imaging quality thereof, thereby further realizing quick and accurate management of the imaging quality thereof so as to facilitate to acquire fetal ultrasound images with high quality, which facilitates the acquisition of accurate fetal growth and development.

In an optional embodiment, the method further comprises: after acquiring the targeted features of the fetal ultrasound images, detecting whether or not abnormal features exist at the targeted features in the fetal ultrasound images, when they exist, confirming that the chapter where the abnormal features locate is the location of abnormal features, wherein the location comprises at least one of a chapter, a cross-section, and a part.

In the optional embodiment, further and optionally, outputting the location of the abnormal feature to authorized personnel, after identifying the location of the abnormal feature.

For example, when an abnormality of lateral ventricle (e.g., hydrocephalus etc.) is detected, identifying the chapter in which the lateral ventricle is located as an abnormal chapter, and outputting the abnormal featured chapter to authorized personnel.

In the optional embodiment, further and optionally, when multiple abnormal features exist, identifying an optimal location for an abnormal feature from all the locations of the abnormal features corresponding to the multiple abnormal features, which is exemplified by an optimal chapter for the abnormal features; further, when abnormal features exist, multiplying the score corresponding to the location of the abnormal features by a predetermined coefficient (e.g., ten) as the final score corresponding to the location of the abnormal features, and acquiring the location of the abnormal features with the highest score as the optimal location for the abnormal features.

In the optional embodiment, regarding the relevant description for targeted feature of fetal ultrasound images, please refer to the detailed description of the relevant content in the First Embodiment, which is not repeated hereby.

Obviously, In the optional embodiment, identifying the location of abnormal features after detecting that the abnormal features exist at the targeted features of the fetal ultrasound images, which is exemplified by an optimal chapter for the abnormal features; outputting the location to authorized personnel so as to facilitate authorized personnel to a quick identification and localization of the abnormal features.

In step 204, identifying the imaging quality of the fetal ultrasound images based on combining the imaging score thereof and the detecting result corresponding to the fetal ultrasound images.

In the present embodiment of the invention, regarding the description for step 201, step 202 and step 204, please refer to the detailed description of steps from 101 to 103 in the First Embodiment, which is not repeated hereby.

Obviously, the implementation of the method for identification of imaging quality of fetal ultrasound images, as described in FIG. 2, may lead to a quick and accurate identification of the imaging quality of fetal ultrasound images, by identifying automatically the imaging quality thereof based on the imaging score thereof, thereby realizing a quick and accurate management of the imaging quality thereof so as to facilitate to acquire fetal ultrasound images with high quality, which facilitates the acquisition of accurate fetal growth and development, which may have an acknowledgment of the operational standardization of the personnel during the detection of fetal ultrasound images and may have an acknowledgment whether or not all the required detected items for fetus have been finished. Additionally, it may further improve the identified accuracy for the imaging quality of fetal ultrasound images, by identifying automatically the imaging quality thereof combining the imaging score thereof and the detecting result, thereby further realizing a quick and accurate management of the imaging quality thereof.

Third Embodiment

The present embodiment of the invention discloses a method for identification of imaging score for fetal ultrasound images. The method may be applied in a server (service device) for identification of imaging quality, wherein the server therefor may include a local server therefor or a cloud server therefor, which is not limited herein. The method for identification of imaging score for fetal ultrasound images may comprise:

At step 1, dividing the fetal ultrasound images into chapters, and acquiring at least a targeted chapter.

In the present embodiment of the invention, the fetal ultrasound images comprise multiple consecutive frames of fetal ultrasound sub-images.

In the present embodiment of the invention, each targeted chapter comprising a plurality of consecutive frames of the fetal ultrasound sub-images, all the fetal ultrasound sub-images included in each targeted chapter differing from each other, a collective amount of all the fetal ultrasound sub-images included in each targeted chapter equaling to a collective amount of all the fetal ultrasound sub-images included in the fetal ultrasound images.

At step 2, computing a score for the targeted chapter based on parameters of targeted features of each frame of the fetal ultrasound sub-images included in each targeted chapter.

In the present embodiment of the invention, for each frame of the fetal ultrasound sub-images, the targeted features comprising at least one of a part feature, a structural feature or a cross-sectional feature.

At step 3, confirming the score for all the targeted chapters as the imaging score for the fetal ultrasound images.

It is to be noted that, regarding the relevant description from step 1 to step 3, please refer to the detailed description of the relevant content in the First Embodiment and the Second Embodiment, which is not repeated hereby.

Obviously, the implementation of the method for identification of imaging quality of fetal ultrasound images may automatically divide the fetal ultrasound images into chapters with different categories and compute the score of each chapter as the imaging score of the fetal ultrasound images, which may improve the acquired accuracy and acquired efficiency for the imaging score thereof, so as to facilitate to improve the identified accuracy and identified reliability for the imaging quality thereof, thereby realizing a quick and accurate management of the imaging quality thereof so as to facilitate to acquire the fetal ultrasound images with high quality, which facilitates to improve the identified accuracy and identified reliability of the fetal growth and development.

Fourth Embodiment

Figure 3:
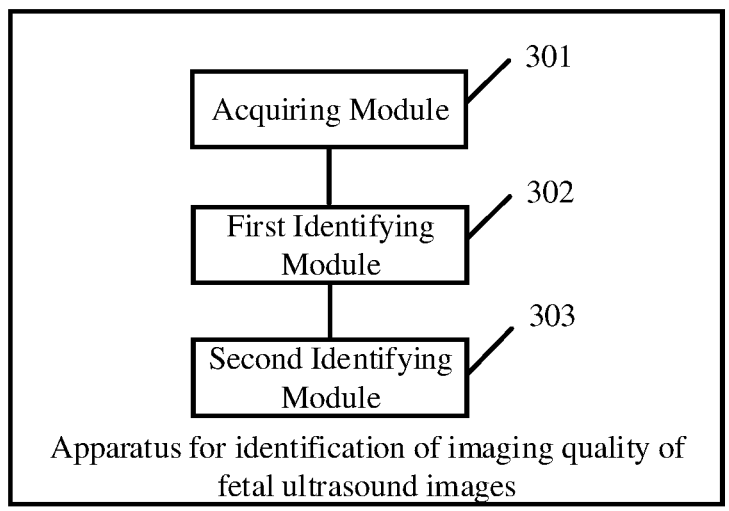
FIG. 3 is a structural diagram of a first apparatus for identification of imaging quality of fetal ultrasound images, as disclosed in embodiments of the present invention.

Please refer to FIG. 3, which is a structural diagram of a first apparatus for identification of imaging quality of fetal ultrasound images, as disclosed in embodiments of the present invention. As shown in FIG. 3 the first apparatus for identification of imaging quality of fetal ultrasound images may be applied in a server (service device) for identification of imaging quality, wherein the server therefor may include a local server therefor or a cloud server therefor, which is not limited herein. As shown in FIG. 3 the first apparatus for identification of imaging quality of fetal ultrasound images may comprise an acquiring module 301, used for acquiring parameters of fetal ultrasound images, used for identification of imaging quality of fetal ultrasound images; a first identifying module 302, used for identifying an imaging score of fetal ultrasound images based on the parameters thereof; and a second identifying module 303, used for identifying the imaging quality thereof based on the imaging score thereof.

Obviously, the implementation of the apparatus for identification of imaging quality of fetal ultrasound images, as described in FIG. 3, may lead to a quick and accurate identification of the imaging quality of fetal ultrasound images, by identifying automatically the imaging quality thereof based on the imaging score thereof, thereby realizing a quick and accurate management of the imaging quality thereof so as to facilitate to acquire fetal ultrasound images with high quality, which facilitates the acquisition of accurate fetal growth and development and may have an acknowledgment of the operational standardization of the personnel during the detection of fetal ultrasound images.

In an optional embodiment, the acquiring module 301 acquires the parameter of fetal ultrasound images, specifically, by: inputting fetal ultrasound images into a predetermined parameter-identifying model for analysis and acquiring an analyzed result outputted by the parameter-identifying model as the parameters of fetal ultrasound images, the parameter-identifying model including a feature-identifying model and/or a cross-section-identifying model, wherein, for fetal ultrasound images, when the parameter-identifying model is the feature-identifying model, the parameters include featured parameters, the featured parameters include a part featured parameter and/or a structural featured parameter; when the parameter-identifying model is the cross-section-identifying model, the parameters include cross-sectional parameters, and the cross-sectional parameters include a cross-sectional score for a standard cross-section; and/or, receiving parameters regarding fetal ultrasound images sent by a predetermined terminal device and/or inputted by an authorized person as the parameters of ultrasound images, wherein, for fetal ultrasound images, the parameters include the featured parameters and/or cross-sectional parameters, the featured parameters include a part feature parameter and/or a structural feature parameter; and the cross-sectional parameters include a cross-sectional score for the standard cross-section.

Obviously, the implementation of the apparatus, as described in FIG. 3, may automatically and quickly, without manual involvement, acquire the parameter of the fetal ultrasound images by inputting the fetal ultrasound images into the parameter-identifying model for analysis, which may improve the acquired accuracy and acquired reliability for the parameter of the fetal ultrasound images, so as to improve the identified accuracy and identified efficiency for the imaging score of the fetal ultrasound images; the parameter of the fetal ultrasound images may be acquired by being sent by the terminal device and or being inputted by the authorized personnel, which may enrich the acquisition means of the parameter of the fetal ultrasound images.

Figure 4:
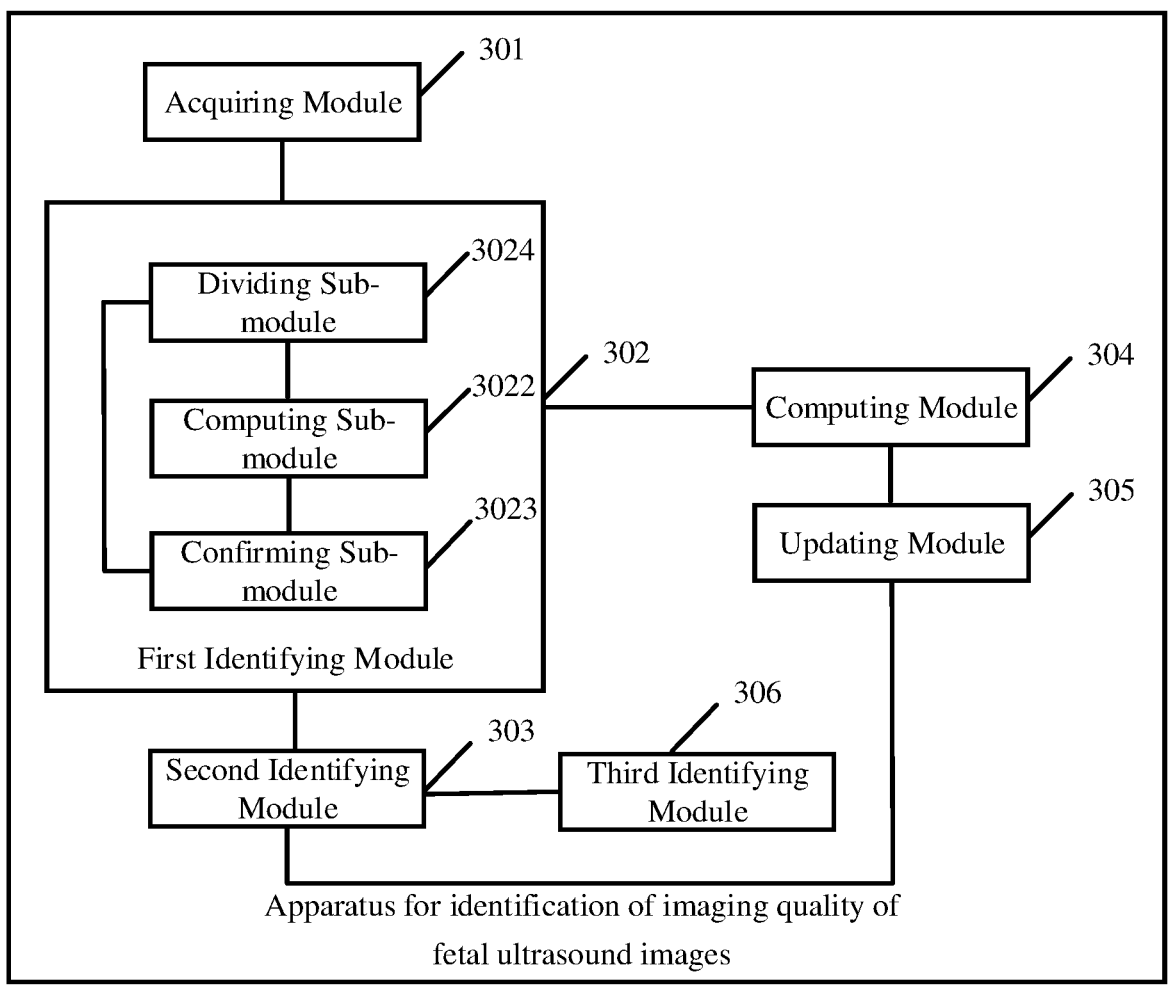
FIG. 4 is a structural diagram of a second apparatus for identification of imaging quality of fetal ultrasound images, as disclosed in embodiments of the present invention.

In an optional embodiment, the aforementioned fetal ultrasound images comprise multiple consecutive frames of fetal ultrasound sub-images. As shown in FIG. 4, the first identifying module 302 may comprise a dividing sub-module 3021, used for dividing the fetal ultrasound images into chapters, and acquiring at least a targeted chapter, each targeted chapter comprising a plurality of consecutive frames of the fetal ultrasound sub-images, all the fetal ultrasound sub-images included in each targeted chapter differing from each other, a collective amount of all the fetal ultrasound sub-images included in each targeted chapter equaling to a collective amount of all the fetal ultrasound sub-images included in the fetal ultrasound images; a computing sub-module 3022, used for computing a score for the targeted chapter based on parameters of targeted features of each frame of the fetal ultrasound sub-images included in each targeted chapter, for each frame of the fetal ultrasound sub-images, the targeted features comprising at least one of a part feature, a structural feature or a cross-sectional feature; and a confirming sub-module 3023, used for confirming the score for all the targeted chapters as the imaging score for the fetal ultrasound images.

In the optional embodiment, the fetal ultrasound images correspond to at least one targeted category, the targeted category comprising a feature category or a cross-sectional category, an amount of a targeted feature corresponding to each targeted category being greater than or equal to one; when the targeted category is the featured category, the targeted feature includes a part feature or a structural feature; when the targeted category is a cross-sectional category, the targeted feature includes a standard cross-section; and each of the targeted category corresponds to at least one frame of the fetal ultrasound sub-images, all the fetal ultrasound sub-images corresponding to each targeted category differing from each other, all the fetal ultrasound sub-images corresponding to all the targeted category constituting the fetal ultrasound images.

Obviously, the implementation of the apparatus, as described in FIG. 4, may compute the score of each chapter as the imaging score of the fetal ultrasound images by automatically dividing the fetal ultrasound images into chapters with different categories, which may improve the acquired accuracy and acquired efficiency of the imaging score of the fetal ultrasound images, so as to facilitate to improve the identified accuracy and identified reliability of the imaging quality of the fetal ultrasound images, thereby facilitating the acquisition of the fetal ultrasound images with high quality.

In an optional embodiment, as shown in FIG. 4, division of the fetal ultrasound images into chapters through the dividing sub-module 3021, and acquisition of at least a targeted chapter comprises specifically: identifying, for each targeted category included in the fetal ultrasound images, a starting frame and an ending frame of the fetal ultrasound sub-images; confirming, for each targeted category, all the fetal ultrasound sub-images of the starting frame, the ending frame and all frames between the starting frame and the ending frame, as the targeted chapter corresponding to each targeted category; and for each targeted category corresponding to the fetal ultrasound sub-images, the starting frame of the fetal ultrasound sub-images is where the fetal ultrasound sub-images with the targeted feature of the targeted category first show in the fetal ultrasound images, and the ending frame of the fetal ultrasound sub-images is where the fetal ultrasound sub-images with the targeted feature of the targeted category last show in the fetal ultrasound images or where a predetermined amount of frames of the fetal ultrasound sub-images shows consecutively after the starting frame of the fetal ultrasound sub-images with the targeted feature of the targeted category.

Obviously, the implementation of the apparatus, as described in FIG. 4, may realize the automated identification of the chapter corresponding to each part feature, structural feature, or standard cross-section by automatically identifying the starting frame and ending frame of the fetal ultrasound images of each part feature, structural feature, or standard cross-section, which may improve the identified efficiency and identified accuracy of each chapter, thereby improving the computed efficiency and computed accuracy of the score of each chapter.

In an optional embodiment, as shown in FIG. 4, computation of the score for the targeted chapter through the computing sub-module 3022 based on the parameters of targeted features of each frame of the fetal ultrasound sub-images included in each targeted chapter comprises specifically: computing a sum of the score for part features of each fetal ultrasound sub-image included in each targeted chapter, as the score for the targeted chapter, when the targeted feature, in each frame of the fetal ultrasound sub-images, is the part feature thereof; computing the score for the targeted chapter based on a probability of category, a probability of location and a weighted value for the structural feature of each frame of fetal ultrasound sub-images included in each targeted chapter, when the targeted feature, in each frame of the fetal ultrasound sub-images, is the structural feature thereof; and computing a sum of the score for cross-sections of the standard cross-section of each fetal ultrasound sub-image included in each targeted chapter, as the score for the targeted chapter, when the targeted feature, in each frame of the fetal ultrasound sub-images, is a standard cross-section thereof.

Obviously, the implementation of the apparatus, as described in FIG. 4, may not only realize the identification of the score for chapters but also enrich the identification means of the score of chapters by respectively computing the score of each structural feature, part feature, or cross-sectional feature, which improves the identified accuracy and reliability of the score of chapters; the imaging quality of the fetal ultrasound images is identified by combining the score of chapters from the score of the structural feature, part feature, and cross-sectional feature, which may further improve the identified accuracy and reliability of the imaging quality of the fetal ultrasound images, thereby facilitating the acquisition of the fetal ultrasound images with high quality.

In an optional embodiment, as shown in FIG. 4, the apparatus further comprises a computing module 304 and an updating module 305; the confirming sub-module 3023 is further used for identification of a total number of frames of the fetal ultrasound sub-images included in each targeted chapters, after division of the fetal ultrasound images into chapters through the dividing sub-module 3021 and acquisition of at least a targeted chapter; the computing module 304 is used for dividing the score for each targeted chapter by the total number of frames of all the fetal ultrasound sub-images included in the targeted chapter to acquire a targeted score for the targeted chapter, after computation of the score for the targeted chapter through the first identifying module 302 based on the parameters of targeted features of each frame of the fetal ultrasound sub-images included in each targeted chapter; and the updating module 305 is used for updating the score for each targeted chapter as the targeted score for the targeted chapter, and triggering the second identifying module 303 to confirm the score for all the targeted chapters as the imaging score for the fetal ultrasound images.

In the optional embodiment, the confirming sub-module 3023 may be triggered to confirm the total frames of all the fetal ultrasound sub-images included in each targeted chapter, after the division into chapters through the dividing sub-module 3021 and the acquisition of at least one targeted chapter.

Obviously, the implementation of the apparatus, as described in FIG. 4, may acquire a new score and update the new score as the imaging score of the fetal ultrasound images based on the score of the chapter and the total frames of the chapter after acquiring the score of the chapter, which may further improve the identified accuracy for the imaging quality of the fetal ultrasound images, thereby realizing a quick and accurate management of the imaging quality thereof.

In an optional embodiment, as shown in FIG. 4, identification for the imaging score for the fetal ultrasound images through the first identifying module 302 based on the parameters thereof comprises specifically: confirming the score for part features of the fetal ultrasound images as the imaging score thereof, when the parameter of the fetal ultrasound images is the part feature parameter thereof, the part feature parameter thereof comprising the score for part feature thereof; and/or, when the parameter of the fetal ultrasound images is the structural feature parameter thereof, the structural feature parameter thereof comprises the probability of category, the probability of location, and the weighted value of the structural feature thereof; computing the score for the structural feature based on the probability of category, the probability of location, and the weighted value of the structural feature of the fetal ultrasound images, and confirming the score for the structural feature as the imaging score for the fetal ultrasound images; and/or when the parameter of the fetal ultrasound images is the featured parameters thereof, the structural feature parameter thereof comprises the probability of category, the probability of location, and the weighted value of the structural feature thereof, and the part feature parameter thereof comprises a probability of category of the part feature of the fetal ultrasound images; computing the score for the structural feature based on the probability of category of the part feature, the probability of category, the probability of location, and the weighted value of the structural feature of the fetal ultrasound images, and confirming the score for the structural feature as the imaging score for the fetal ultrasound images; and/or, identifying the standard cross-section of the fetal ultrasound images based on the probability of category of the part feature, and the probability of category of the structural feature; and computing the cross-sectional score for the standard cross-section of the fetal ultrasound images based on the parameters of the structural features in the standard cross-section of the fetal ultrasound images as the imaging score for the fetal ultrasound images, the parameter of structural features of the fetal ultrasound images comprising the parameter of structural features in the standard cross-section of the fetal ultrasound images.

Obviously, the implementation of the apparatus, as described in FIG. 4, may realize computation of the score for the fetal ultrasound images by respectively computing the score for part feature, structural feature and cross-sectional feature of the fetal ultrasound images, which may enrich the identification means of the score of the fetal ultrasound images, so as to improve the identified accuracy for the imaging quality of the fetal ultrasound images, thereby realizing a quick and accurate management of the imaging quality thereof.

In an optional embodiment, as shown in FIG. 4, the apparatus further comprises: a third identifying module 306, used for, before identification for the imaging quality of the fetal ultrasound images through the second identifying module 303 based on the imaging score thereof, identifying a detecting result corresponding to the fetal ultrasound images, used for identification for the imaging quality of the fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections; and the identification for the imaging quality of the fetal ultrasound images through the second identifying module 303 based on the imaging score thereof comprises specifically: identifying the imaging quality of the fetal ultrasound images based on combining the imaging score thereof and the detecting result corresponding to the fetal ultrasound images.

Obviously, the implementation of the apparatus, as described in FIG. 4, may further confirm the imaging quality of the fetal ultrasound images based on combining the imaging score thereof and the detecting result by acquiring the detecting result of the fetal ultrasound image, such as:

whether or not all the required detected standard cross-section have been done; which may lead to accurate identification of the imaging quality of fetal ultrasound images, thereby realizing a quick and accurate management of the imaging quality thereof so as to facilitate to acquire fetal ultrasound images with high quality, which facilitates the acquisition of accurate fetal growth and development.

Fifth Embodiment

Figure 5:
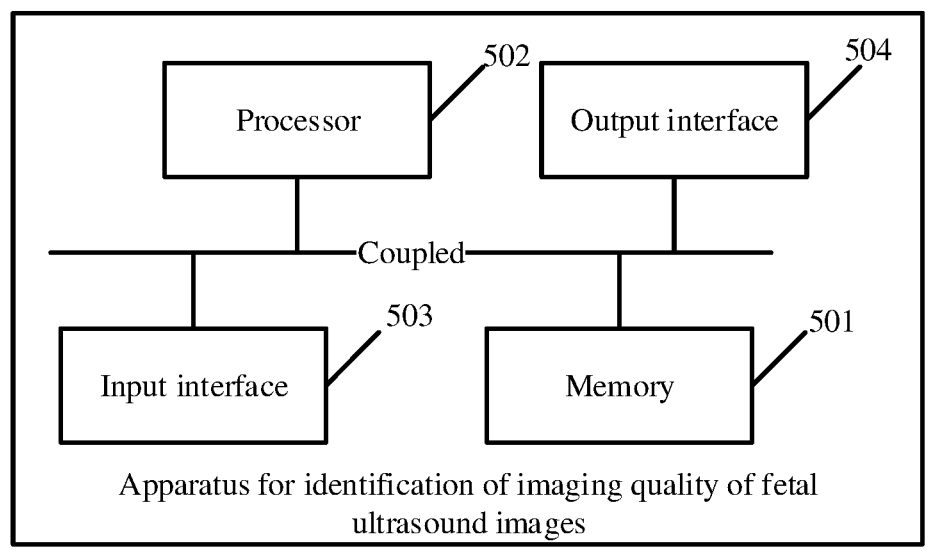
FIG. 5 is a structural diagram of a third apparatus for identification of imaging quality of fetal ultrasound images, as disclosed in embodiments of the present invention.

Please refer to FIG. 5, which is a third apparatus for identification of imaging quality of fetal ultrasound images, as disclosed in embodiments of the present invention. As shown in FIG. 5, the third apparatus for identification of imaging quality of fetal ultrasound images may be applied in a server (service device) for identification of imaging quality, wherein the server therefor may include a local server therefor or a cloud server therefor, which is not limited herein. As shown in FIG. 5, the apparatus for identification of imaging quality of fetal ultrasound images may comprise a memory 501 memorized with an executable program; and a processor 502 coupled with the memory 501; or may further comprise an input interface 503 and an output interface 504 coupled with the processor 502; wherein the processor 502, calling the executable program memorized in the memory 501, implements part of or all of the method for identification of imaging quality of fetal ultrasound images described by the First Embodiment or the Second Embodiment.

Sixth Embodiment

The present embodiment of the invention discloses a computer-readable memory medium that memorizes a computer program for electronic data interchange, wherein the computer program enables the computer to implement part of or all of the method for identification of imaging quality of fetal ultrasound images, described by the First Embodiment or the Second Embodiment.

Seventh Embodiment

The present embodiment of the invention discloses a computer program product comprising a non-instantaneous computer readable memory medium memorized with a computer program, the computer program enabling the computer to implement part of or all of the steps in the method for identification of imaging quality of fetal ultrasound images, described in the First Embodiment or the Second Embodiment.

It is only schematic to describe the aforementioned embodiment of the apparatus. The modules described as separate components may or may not be physically separated, and the modules used as components for display may or may not be physical modules, that is, they may be located in the same place or may be distributed to a plurality of network modules. Some or all of these modules may be selected according to practical demands to achieve the purpose of the solution of the present embodiment. It may be understood and implemented by a person of ordinary skill in the art without inventive effort.

With the specific description of the above embodiments, it is clear to those skilled in the art that the various implementations may be implemented with the aid of software plus the necessary common hardware platform, and of course, with the aid of hardware. Based on this understanding, the above technical solutions that essentially or contribute to the prior art may be embodied in the form of a software product which may be memorized in a computer-readable memory medium, the memory medium including Read-Only Memory, Random Access Memory, Programmable Read-only Memory, Erasable Programmable Read Only Memory, One-time Programmable Read-Only Memory, Electrically-Erasable Programmable Read-Only Memory, Compact Disc Read-Only Memory, other Compact Disc Memory, Disk Memory, Tape Memory or any other computer-readable medium that may be used to carry or memorize data.

Finally, it should be noted that the method and apparatus for identification of fetal cross-section based on ultrasound dynamic images disclosed in the embodiments of the present invention are only preferred embodiments of the present invention, and are only used to illustrate the technical solutions of the present invention, but not to limit them. Despite the detailed description of the invention with reference to the aforementioned embodiments, it should be understood, by those skilled in the art, that the technical solutions recorded in the aforementioned embodiments may still be modified, or equivalent substitutions for some of the technical features thereof may be made; which the essence of the corresponding technical solutions of these modifications or substitutions is without departing from the spirit and scope of the technical solutions of the various embodiments of the invention.

The invention claimed is:

1. A method for identification of imaging quality of a series of fetal ultrasound images, wherein the method is applied to a server for identification of imaging quality using an apparatus for identification of imaging quality of the series of fetal ultrasound images, the method comprising:

acquiring, by an acquiring module of the apparatus for identification of imaging quality of the series of fetal ultrasound images, parameters of the series of fetal ultrasound images, the parameters being configured to identify imaging quality of the series of fetal ultrasound images, wherein the series of fetal ultrasound images comprise multiple consecutive frames of fetal ultrasound sub-images, and each frame of the fetal ultrasound sub-images corresponds to one image of the series of fetal ultrasound images;

identifying, by a first identifying module of the apparatus for identification of imaging quality of the series of fetal ultrasound images, an imaging score of the series of fetal ultrasound images based on the parameters thereof;

wherein the identifying the imaging score of the series of fetal ultrasound images based on the parameters thereof, comprises:

dividing, by a dividing sub-module of the apparatus for identification of imaging quality of the series of fetal ultrasound images, the series of fetal ultrasound images into chapters, and acquiring at least a target chapter, wherein each target chapter comprises multiple consecutive frames of the fetal ultrasound sub-images, and all the fetal ultrasound sub-images included in each target chapter differ from each other;

computing, by a computing sub-module of the apparatus for identification of imaging quality of the series of fetal ultrasound images, based on parameters of a target feature of each frame of the fetal ultrasound sub-images included in each target chapter, a score of the target chapter, wherein the target feature with respect to each frame of the fetal ultrasound sub-images comprising at least one of a part feature, a structural feature or a cross-sectional feature, wherein the computing the score of the target chapter, comprises:

computing, by the computing sub-module of the apparatus for identification of imaging quality of the series of fetal ultrasound images, a sum of the score, from part features of each fetal ultrasound sub-image included in each target chapter, as the score of the target chapter, when the target feature, in each frame of the fetal ultrasound sub-images, is the part feature thereof;

computing, by the computing sub-module of the apparatus for identification of imaging quality of the series of fetal ultrasound images, based on a probability of category, a probability of location, and a weighted value for the structural feature of each frame of fetal ultrasound sub-images included in each target chapter, the score of the target chapter, when the target feature, in each frame of the fetal ultrasound sub-images, is the structural feature thereof;

computing, by the computing sub-module of the apparatus for identification of imaging quality of the series of fetal ultrasound images, a sum of the score, from cross-sections of a standard cross-section of each fetal ultrasound sub-image included in each target chapter, as the score of the target chapter, when the target feature, in each frame of the fetal ultrasound sub-images, is a standard cross-section thereof;

confirming, by a confirming sub-module of the apparatus for identification of imaging quality of the series of fetal ultrasound images, the score for all the target chapters as the imaging score of the series of fetal ultrasound images,-and identifying, by a second identifying module of the apparatus for identification of imaging quality of the series of fetal ultrasound images, the imaging quality of the series of fetal ultrasound images based on the imaging score thereof.

2. The method for identification of imaging quality of the series of fetal ultrasound images according to claim 1, wherein the acquiring the parameters of the fetal ultrasound images comprises:

inputting fetal ultrasound images into a predetermined parameter-identifying model for analysis and acquiring an analyzed result outputted by the parameter-identifying model as the parameters of fetal ultrasound images, the parameter-identifying model including a feature-identifying model and/or a cross-section-identifying model, wherein, for fetal ultrasound images, when the parameter-identifying model is the feature-identifying model, the parameters include featured parameters, the featured parameters include a part featured parameter and/or a structural featured parameter; when the parameter-identifying model is the cross-section-identifying model, the parameters include cross-sectional parameters, and the cross-sectional parameters include a cross-sectional score of a standard cross-section; and/or receiving parameters of the series of fetal ultrasound images sent by a predetermined terminal device and/or inputted by an authorized person as the parameters of the series of fetal ultrasound images, wherein, for the series of fetal ultrasound images, the parameters include the featured parameters and/or cross-sectional parameters, the featured parameters include a part feature parameter and/or a structural feature parameter; and the cross-sectional parameters include a cross-sectional score of a standard cross-section.

3. The method for identification of imaging quality of the series of fetal ultrasound images according to claim 1, wherein a collective amount of all the fetal ultrasound sub-images included in each target chapter equaling to a collective amount of all the fetal ultrasound sub-images included in the series of fetal ultrasound images.

4. The method for identification of imaging quality of the series of fetal ultrasound images according to claim 3, wherein the fetal ultrasound images correspond to at least one target category, the target category comprising a feature category or a cross-sectional category, an amount of a target feature corresponding to each target category being greater than or equal to one;

when the target category is the featured category, the target feature includes a part feature or a structural feature;

when the target category is a cross-sectional category, the target feature includes a standard cross-section; and each of the target category corresponds to at least one frame of the fetal ultrasound sub-images, all the fetal ultrasound sub-images corresponding to each target category differing from each other, all the fetal ultrasound sub-images corresponding to all the target category constituting the series of fetal ultrasound images.

5. The method for identification of imaging quality of the series of fetal ultrasound images according to claim 4, wherein the dividing the fetal ultrasound images into chapters and the acquiring at least a target chapter comprises:

identifying, for each target category included in the series of fetal ultrasound images, a starting frame and an ending frame of the fetal ultrasound sub-images;

confirming, for each target category, all the fetal ultrasound sub-images of the starting frame, the ending frame and all frames between the starting frame and the ending frame, as the target chapter corresponding to each target category; and for each target category corresponding to the fetal ultrasound sub-images, the starting frame of the fetal ultrasound sub-images is where the fetal ultrasound sub-images with the target feature of the target category first show in the series of fetal ultrasound images, and the ending frame of the fetal ultrasound sub-images is where the fetal ultrasound sub-images with the target feature of the target category last show in the fetal ultrasound images or where a predetermined amount of frames of the fetal ultrasound sub-images shows consecutively after the starting frame of the fetal ultrasound sub-images with the target feature of the target category.

6. The method for identification of imaging quality of the series of fetal ultrasound images according to claim 3, after the dividing the fetal ultrasound images into chapters and acquisition of at least a target chapter, the method further comprising:

identifying a total number of frames of the fetal ultrasound sub-images included in each target chapter;

after the computing the score for the target chapter based on the parameters of target features of each frame of the fetal ultrasound sub-images included in each target chapter, the method further comprising:

dividing the score for each target chapter by the total number of frames of all the fetal ultrasound sub-images included in the target chapter to acquire a target score for the target chapter;
updating the score for each target chapter as the target score for the target chapter, and
confirming the score for all the target chapters as the imaging score for the fetal ultrasound images.

7. The method for identification of imaging quality of the series of fetal ultrasound images according to claim 2, wherein the identifying the imaging score for the fetal ultrasound images based on the parameters thereof comprises:
confirming the score for part features of the series of fetal ultrasound images as the imaging score thereof, when the parameter of the series of fetal ultrasound images is the part feature parameter thereof, the part feature parameter thereof comprising the score of part feature thereof; and/or,
when the parameter of the series of fetal ultrasound images is the structural feature parameter thereof, the structural feature parameter thereof comprises a probability of category, a probability of location, and a weighted value of the structural feature thereof;
computing, based on the probability of category, the probability of location, and the weighted value of the structural feature of the fetal ultrasound images, the score for the structural feature, and confirming the score for the structural feature as the imaging score of the series of fetal ultrasound images; and/or,
when the parameter of the series of fetal ultrasound images is the featured parameters thereof, the structural feature parameter thereof comprises the probability of category, the probability of location, and the weighted value of the structural feature thereof, and the part feature parameter thereof comprises a probability of category of the part feature of the series of fetal ultrasound images;
computing, based on the probability of category of the part feature, the probability of category, the probability of location, and the weighted value of the structural feature of the series of fetal ultrasound images, the score of the structural feature, and confirming the score for the structural feature as the imaging score of the series of fetal ultrasound images; and/or,
identifying, based on the probability of category of the part feature, and the probability of category of the structural feature, the standard cross-section of the series of fetal ultrasound images; and
computing, based on the parameters of the structural features in the standard cross-section of the fetal ultrasound images, the cross-sectional score of the standard cross-section of the fetal ultrasound images as the imaging score of the series of fetal ultrasound images, the parameter of structural features of the series of fetal ultrasound images comprising the parameter of structural features in the standard cross-section of the series of fetal ultrasound images.

8. The method for identification of imaging quality of the series of fetal ultrasound images according to claim 1, before the identifying the imaging quality of the series of fetal ultrasound images based on the imaging score thereof, the method further comprising:
identifying a detecting result corresponding to the fetal ultrasound images, used for identification for the imaging quality of the series of fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections;
the identifying the imaging quality of the series of fetal ultrasound images based on the imaging score thereof comprises:
identifying the imaging quality of the series of fetal ultrasound images based on combining the imaging score thereof and the detecting result corresponding to the series of fetal ultrasound images.

9. The method for identification of imaging quality of the series of fetal ultrasound images according to claim 2, before the identifying the imaging quality of the fetal ultrasound images based on the imaging score thereof, the method further comprising:
identifying a detecting result corresponding to the fetal ultrasound images, used for identification for the imaging quality of the series of fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections;
the identifying the imaging quality of the series of fetal ultrasound images based on the imaging score thereof comprises:
identifying the imaging quality of the series of fetal ultrasound images based on combining the imaging score thereof and the detecting result corresponding to the series of fetal ultrasound images.

10. The method for identification of imaging quality of the series of fetal ultrasound images according to claim 3, before the identifying the imaging quality of the fetal ultrasound images based on the imaging score thereof, the method further comprising:
identifying a detecting result corresponding to the fetal ultrasound images, used for identification for the imaging quality of the series of fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections;
the identifying the imaging quality of the series of fetal ultrasound images based on the imaging score thereof comprises:
identifying the imaging quality of the series of fetal ultrasound images based on combining the imaging score thereof and the detecting result corresponding to the series of fetal ultrasound images.

11. The method for identification of imaging quality of the series of fetal ultrasound images according to claim 4, before the identifying the imaging quality of the fetal ultrasound images based on the imaging score thereof, the method further comprising:
identifying a detecting result corresponding to the fetal ultrasound images, used for identification for the imaging quality of the series of fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections;

the identifying the imaging quality of the series of fetal ultrasound images based on the imaging score thereof comprises:
identifying the imaging quality of the series of fetal ultrasound images based on combining the imaging score thereof and the detecting result corresponding to the series of fetal ultrasound images.

12. The method for identification of imaging quality of the series of fetal ultrasound images according to claim 5, before the identifying the imaging quality of the fetal ultrasound images based on the imaging score thereof, the method further comprising:
identifying a detecting result corresponding to the fetal ultrasound images, used for identification for the imaging quality of the series of fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections;
the identifying the imaging quality of the series of fetal ultrasound images based on the imaging score thereof comprises:
identifying the imaging quality of the series of fetal ultrasound images based on combining the imaging score thereof and the detecting result corresponding to the series of fetal ultrasound images.

13. The method for identification of imaging quality of the series of fetal ultrasound images according to claim 6, before the identifying the imaging quality of the fetal ultrasound images based on the imaging score thereof, the method further comprising:
identifying a detecting result corresponding to the fetal ultrasound images, used for identification for the imaging quality of the series of fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections;
the identifying the imaging quality of the series of fetal ultrasound images based on the imaging score thereof comprises:
identifying the imaging quality of the series of fetal ultrasound images based on combining the imaging score thereof and the detecting result corresponding to the series of fetal ultrasound images.

14. The method for identification of imaging quality of the series of fetal ultrasound images according to claim 7, before the identifying the imaging quality of the fetal ultrasound images based on the imaging score thereof, the method further comprising:
identifying a detecting result corresponding to the fetal ultrasound images, used for identification for the imaging quality of the series of fetal ultrasound images, wherein the detecting result corresponding thereto comprises at least one of the results for features, biological diameters, and Doppler blood flow spectra, the feature detecting results comprising at least one of feature detecting results for parts, structures and standard cross-sections;
the identifying the imaging quality of the series of fetal ultrasound images based on the imaging score thereof comprises:
identifying the imaging quality of the series of fetal ultrasound images based on combining the imaging score thereof and the detecting result corresponding to the series of fetal ultrasound images.

15. An apparatus for identification of imaging quality of a series of fetal ultrasound images, comprising:
an acquiring module, configured to acquire parameters of the series of fetal ultrasound images, in which the parameters thereof is configured to identify imaging quality of the series of fetal ultrasound images;
a first identifying module, configured to identify an imaging score of the series of fetal ultrasound images based on the parameters thereof;
wherein the first identifying module comprises:
a dividing sub-module, configured to divide the series of fetal ultrasound images into chapters, and acquire at least a target chapter, wherein each target chapter comprises multiple consecutive frames of the fetal ultrasound sub-images, and all the fetal ultrasound sub-images included in each target chapter differ from each other;
a computing sub-module, configured to compute, based on parameters of a target feature of each frame of the fetal ultrasound sub-images included in each target chapter, a score of the target chapter, wherein the target feature with respect to each frame of the fetal ultrasound sub-images comprising at least one of a part feature, a structural feature or a cross-sectional feature,
wherein the computing sub-module is further configured to:
compute a sum of the score, from part features of each fetal ultrasound sub-image included in each target chapter, as the score of the target chapter, when the target feature, in each frame of the fetal ultrasound sub-images, is the part feature thereof;
compute, based on a probability of category, a probability of location, and a weighted value for the structural feature of each frame of fetal ultrasound sub-images included in each target chapter, the score of the target chapter, when the target feature, in each frame of the fetal ultrasound sub-images, is the structural feature thereof;
compute a sum of the score, from cross-sections of a standard cross-section of each fetal ultrasound sub-image included in each target chapter, as the score of the target chapter, when the target feature, in each frame of the fetal ultrasound sub-images, is a standard cross-section thereof;
a confirming sub-module, configured to confirm the score for all the target chapters as the imaging score of the series of fetal ultrasound images, and
a second identifying module, configured to identify the imaging quality thereof based on the imaging score thereof.

* * * * *